United States Patent [19]

Okuyama et al.

[11] Patent Number: 5,208,035

[45] Date of Patent: May 4, 1993

[54] DICLOFENAC SODIUM PLASTER

[75] Inventors: Hirohisa Okuyama, Tomisatomachi; Yasuo Ikeda, Narashino; Shigenori Otsuka, Chiba; Shuichi Kasai, Narita; Akira Iwasa, Yotsukaido, all of Japan

[73] Assignee: SS Pharmaceutical Co., Ltd., Tokyo, Japan

[21] Appl. No.: 801,901

[22] Filed: Dec. 3, 1991

[30] Foreign Application Priority Data

Jul. 26, 1991 [JP] Japan .................................. 3-187532

[51] Int. Cl.[5] ............................................. A61L 15/16
[52] U.S. Cl. .................................... 424/446; 424/449; 514/946
[58] Field of Search ................. 424/446, 449; 514/946

[56] References Cited

U.S. PATENT DOCUMENTS

| | | | |
|---|---|---|---|
| 4,455,146 | 6/1984 | Noda | 424/449 |
| 4,543,251 | 9/1985 | Kamishita | 424/81 |
| 4,695,465 | 9/1987 | Kigasawa | 424/449 |
| 4,801,458 | 1/1989 | Hidaka | 424/443 |
| 4,855,142 | 8/1989 | Fankhauser | 424/434 |
| 4,931,283 | 6/1990 | Tsuk | 424/449 |
| 4,933,184 | 6/1990 | Tsuk | 514/947 |

FOREIGN PATENT DOCUMENTS 1-197435  8/1989  Japan.
2-49722   2/1990  Japan.

OTHER PUBLICATIONS

Patent Abstracts of Japan, Dec. 21, 1984 & JP-A-59 227 819 (Nitto Denki Kogio KK) *Abstract*.

Primary Examiner—Thurman K. Page
Assistant Examiner—D. Gabrielle Phelan
Attorney, Agent, or Firm—Oblon, Spivak, McClelland, Maier & Neustadt

[57] ABSTRACT

A diclofenac sodium plaster has a backing material and a paste spread on the backing material. The paste is composed of diclofenac sodium, a penetration enhancer composed of 1-menthol and propylene glycol, and a hydrophilic base composed principally of a water-soluble polymer.

3 Claims, 2 Drawing Sheets

DICLOFENAC SODIUM PLASTER

BACKGROUND OF THE INVENTION a) Field of the Invention

The present invention relates to a diclofenac sodium plaster containing diclofenac sodium and having good percutaneous absorption.

b) Description of the Related Art

Diclofenac sodium is a non-steroidal anti-inflammatory analgesic and is now available as oral preparations and suppositories on the market. However, oral or rectal administration involves the problem of various side effects, led by stomach troubles, while suppositories are accompanied by the problem of shock or the like which may be caused by an abrupt increase in the diclofenac concentration in blood. To overcome such problems, formulations for external use, such as ointments, creams and liquid preparations, have been proposed with a view to allowing diclofenac sodium to act locally or on the whole body. In practice, however, there is no external preparation with good percutaneous absorption.

The present inventors previously found that a gel-type ointment having excellent percutaneous absorption can be obtained by adding diclofenac or a salt thereof (and menthol) to a gel-form base which has been obtained by neutralizing a gelling agent with ammonia or an alkylamine, and filed a patent application there-on (Japanese Patent Application Laid-Open No. 49722/1990.

The gel-type ointment is however accompanied by the drawback that, even when a gel-type ointment excellent in percutaneous absorption as described above is used, its stable percutaneous absorption over a long period of time is difficult because the gel-type ointment is prone to separation, for example, due to contact between the skin of an applied part and clothing, washing, or the like. In addition, it is difficult to spread such an ointment in a predetermined constant amount and at a constant thickness on the skin, leading to the further drawback that it is difficult to maintain stable percutaneous absorption over a long time.

The present inventors therefore have proceeded with a further investigation. As a result, the use of a plaster has been found most suitable as a method for extended stable percutaneous absorption of diclofenac.

A paste for plasters, however, is required to have many functions and properties beyond that of carrying an effective ingredient. It is therefore impossible to divert, for example, gel-type ointments which have been employed conventionally. Functions and properties required for a paste for plasters include having suitable adhesiveness when applied to the skin, locational stability during long-term application, easy release from the skin when the plaster is removed, and stability of properties even when stored as a product for a long time. Numerous limitations are therefore imposed on the composition of a paste.

SUMMARY OF THE INVENTION

The present inventors have conducted a still further investigation with a view toward improving the percutaneous absorption of diclofenac from a paste for plaster on which many limitations are imposed as described above. As a result, it has been found that a plaster providing extremely good percutaneous absorption of diclofenac sodium can be obtained by using, as a penetration enhancer to be incorporated in a paste, 1-menthol and propylene glycol in combination and further employing a particular hydrophilic base, leading to the completion of the present invention.

The present invention therefore provides a diclofenac sodium plaster which comprises a backing material and a paste spread on the backing material. The paste comprises diclofenac sodium, a penetration enhancer composed of 1-menthol and propylene glycol, and a hydrophilic base composed principally of a water-soluble polymer.

The diclofenac sodium plaster according to the present invention are extremely good in skin penetration and percutaneous absorption, so that diclofenac sodium can be stably and continuously supplied to an affected part of the body.

DETAILED DESCRIPTION OF THE INVENTION AND PREFERRED EMBODIMENTS

Figure 1:
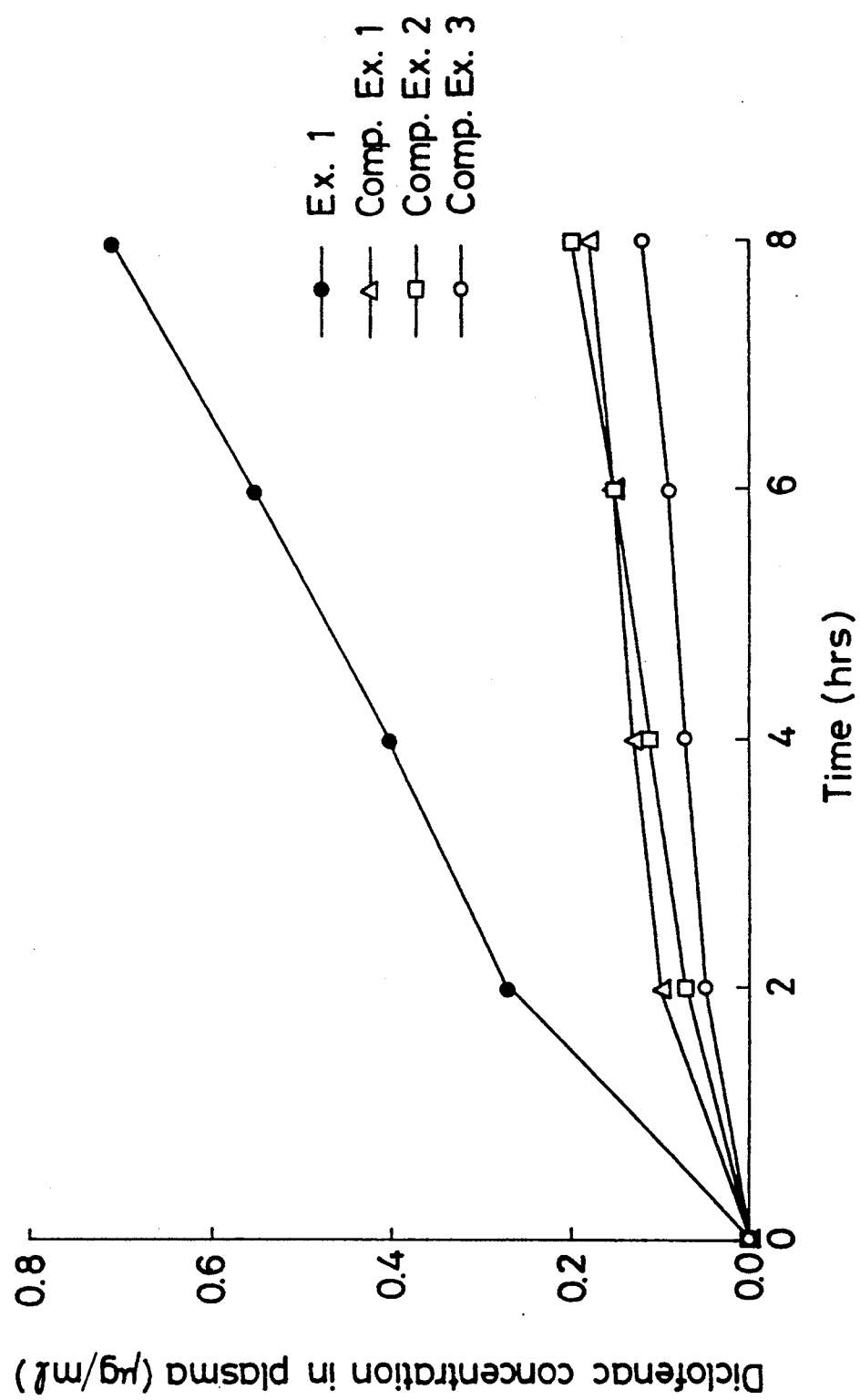
FIG. 1 diagrammatically shows time-dependent changes in the diclofenac concentration in plasma when the diclofenac sodium plasters prepared in Example 1 and Comparative Examples 1-3, respectively, were applied.

Examples of the water-soluble polymer employed as a base in the present invention include polyacrylic acid, sodium polyacrylate, carboxyvinyl polymer, sodium carboxymethylcellulose, polyvinyl pyrrolidone, polyvinyl alcohol, hydroxypropylcellulose, hydroxyethylcellulose, ethylcellulose, alginic acid, sodium alginate, and gelatin. Of these, preferred are those obtained by cross-linking polyacrylic acids and/or polyacrylate salts with multivalent metal compounds and that obtained by freezing and melting an aqueous solution of polyvinyl alcohol. They can be used either singly or in combination. These water-soluble polymers are preferably added in a total proportion of 0.5-40 wt. %, notably 1-20 wt. % based on a paste.

Propylene glycol added as a penetration enhancer is preferably added in a proportion of 0.1-60 wt. % based on the paste, with 0.5-20 wt. % being particularly preferred. 1-Menthol is preferably added in a proportion of 0.05-10 wt. %, especially 0.1-5 wt. % based on the paste.

According to the present invention, the combined use of propylene glycol and 1-menthol as a penetration enhancer can synergistically increase the percutaneous absorption of diclofenac sodium as will be demonstrated in examples to be set forth later. In addition to such a penetration enhancer, the plaster according to the present invention can also include one or more conventional penetration enhancers such as oleic acid, oleyl alcohol, diisopropyl adipate, octyldodecanol, diethyl sebacate, benzyl alcohol, isopropyl myristate, crotamiton, lauryl alcohol, 2-octyldodecanol, ethyl 2-ethylhexanoate, calcium thioglycolate, capric monoglyceride, caprylate esters, caprate esters, decyl oleate, diethyl sebacate, squalane and/or D-limonene.

Besides the essential ingredients described above, the plaster according to the present invention may also include other additives incorporated in conventional hydrophilic-base-containing plasters, for example, polyhydric alcohols as moisturizing agents, such as glycerin and sorbitol; inorganic compounds as fillers, such as kaolin and titanium dioxide; and surfactants such as polyoxyethylene sorbitan monooleate, sorbitan monooleate, polyoxyethylene hydrogenated castor oil, polyoxyethylene lauryl ether and polyoxyethylene monolaurate; as well as, if necessary, perfumes, stabilizers, crosslinking agents, pH regulators, etc.

The plaster according to the present invention can be prepared, preferably, by formulating a paste from the above-described ingredients in a manner known per se in the art and then having the paste carried on a backing material.

The paste useful in the plaster of this invention preferably has a stress in a range of from $5 \times 10^3$ dyne/cm$^2$ to $5 \times 10^5$ dyne/cm$^2$, especially from $0.8 \times 10^4$ dyne/cm$^2$ to $1.0 \times 10^5$ dyne/cm$^2$. Incidentally, the stress of a paste is measured, for example, in the following manner. After the formulation of the paste, it is placed in a cylindrical vessel whose diameter and height are 40 mm and 20 mm, respectively. After sealing the vessel, the vessel with the paste placed therein is maintained at 25° C. for at least 168 hours. The paste is then placed on a sample table of a compression tester (e.g., SUN RHEO METER, trade mark; manufactured by K. K. Sun Kagaku), and its central part is pressed at a compression speed of 300 mm/min against a disk-shaped adapter having a diameter of 15 mm and mounted on a pressure-sensing shaft. The stress of the paste is measured in terms of the stress produced upon pressing the paste over a distance of 2 mm after the adapter has contacted the paste.

No particular limitation is imposed on the backing material as long as it is a woven fabric, non-woven fabric, film or sheet having flexibility. For example, a woven or non-woven fabric of rayon, polyester, polyolefin or polyurethane fibers, a polymer film, a foamed sheet, or the like can be used. They may be applied with an anchor coat, as needed.

No particular limitation is imposed on the preparation method of the plaster according to this invention. The plaster can be prepared by formulating a paste containing 0.5–20 wt. % of diclofenac sodium, spreading it on a backing material and then covering the surface of the paste with a protective film or, as an alternative, by formulating a paste containing 0.5–20 wt. % of diclofenac sodium and then sandwiching it between a backing material and a protective film.

The plaster obtained as described above may be stored in a tight container, envelope or the like, as needed.

The present invention will next be described by examples.

EXAMPLE 1

To 15 g of propylene glycol heated to 40° C. in advance, 1 g of diclofenac sodium, 3 g of l-menthol and 1 g of polyoxyethylene hydrogenated castor oil were added, followed by stirring into an intimate mixture (A). In 10 g of propylene glycol, 2.5 g of sodium carboxymethylcellulose, 6 g of sodium polyacrylate and 0.1 g of aluminum glycinate were uniformly dispersed (B). One gram of gelatin was dissolved in 27.68 g of purified water which had been heated to about 60° C. (C). 0.12 g of tartaric acid, 3.6 g of aqueous polyacrylic acid solution (10%), 30 g of D-sorbitol solution (70% aqueous solution), the mixture (A), the suspension (B) and the solution (C) were kneaded into an intimate paste, which was then spread at a rate of 0.1 g/cm$^2$ on a nonwoven fabric. The surface of the paste was covered with a polyester film, whereby a diclofenac sodium plaster containing 1 mg of diclofenac sodium per cm$^2$ was obtained. The stress of the paste of the diclofenac sodium plaster was $1.8 \times 10^4$ dyne/cm$^2$ when measured by the method described above.

EXAMPLE 2

To 10 g of propylene glycol heated to 40° C. in advance, 1 g of diclofenac sodium, 2 g of benzyl alcohol, 1 g of l-menthol and 1 g of polyoxyethylene hydrogenated castor oil were added, followed by stirring into an intimate mixture (A). In 10 g of propylene glycol, 3 g of sodium carboxymethylcellulose, 5 g of sodium polyacrylate and 0.1 g of dry aluminum ammonium sulfate were uniformly dispersed (B). Four grams of kaolin were evenly dispersed in 10 g of a D-sorbitol solution (70% aqueous solution) (C). 51.9 grams of purified water, 1 g of tartaric acid, the mixture (A), the dispersion (B) and the dispersion (C) were kneaded into an intimate paste, which was then spread at a rate of 0.1 g/cm$^2$ on a non-woven fabric. The surface of the paste was covered with a polyester film, whereby a diclofenac sodium plaster containing 1 mg of diclofenac sodium per cm$^2$ was obtained. The stress of the paste of the diclofenac sodium plaster was $2.7 \times 10^4$ dyne/cm$^2$ when measured by the method described above.

EXAMPLE 3

Two grams of diisopropyl adipate, 1 g of l-menthol and 1 g of polyoxyethylene monolaurate were mixed under stirring while being heated at 40° C. Further, 0.5 g of diclofenac sodium was added, followed by stirring into an intimate mixture (A). Two grams of sodium carboxymethylcellulose, 5 g of sodium polyacrylate and 0.15 g of dry aluminum ammonium sulfate were uniformly dispersed in 15 g of polypropylene glycol (B). One gram of gelatin was dissolved in 38.23 g of purified water which had been heated to about 60° C. (C). 30 grams of a D-sorbitol solution (70% aqueous solution), 0.12 g of tartaric acid, 4 g of an aqueous polyacrylic acid solution (10%), the mixture (A), the dispersion (B), and the solution (C) were kneaded into an intimate paste, which was then spread at a rate of 0.1 g/cm$^2$ on a nonwoven fabric. The surface of the paste was covered with a polypropylene film, whereby a diclofenac sodium plaster containing 0.5 mg of diclofenac sodium per cm$^2$ was obtained. The stress of the paste of the diclofenac sodium plaster was $0.8 \times 10^5$ dyne/cm$^2$ when measured by the method described above.

EXAMPLE 4

13.5 grams of polyvinyl alcohol were dissolved in 76.5 g of purified water which had been heated to 90° C. After the former was dissolved in the latter, the resultant solution was cooled to room temperature (A). While 5 g of propylene glycol was being heated to 40° C., 1 g of diclofenac sodium was dissolved therein, followed by the addition of 1 g of l-menthol (B). The solutions (A) and (B) were combined and stirred into an intimate solution. The solution was then subjected to a centrifugator to deaerate the same. The solution so deaerated was poured at a rate of 0.1 g/cm$^2$ into a mold and then hermetically sealed. The mold with the solution filled therein was stored for 24 hours in a freezer controlled at −20° C., whereby the solution was lyophilized. The lyophilizate so formed was thawed at 10° C. and the resulting sheet was then taken out. The sheet was sandwiched between polyurethane sheets, whereby a diclofenac sodium plaster containing 1 mg of diclofenac sodium per cm$^2$ was obtained. The stress of the paste of the diclofenac sodium plaster was $1.6 \times 10^4$ dyne/cm$^2$ when measured by the method described above.

COMPARATIVE EXAMPLE 1

A diclofenac sodium plaster containing 1 mg of diclofenac sodium per cm$^2$ was obtained in a similar manner to Example 1 except for the addition of concentrated glycerin instead of propylene glycol.

COMPARATIVE EXAMPLE 2

A diclofenac sodium plaster containing 1 mg of diclofenac sodium per cm$^2$ was obtained in a similar manner to Example 1 except for the addition of purified water in place of 1-menthol.

COMPARATIVE EXAMPLE 3

A diclofenac sodium plaster containing 1 mg of diclofenac sodium per cm$^2$ was obtained in a similar manner to Example 1 except that concentrated glycerin and purified water were added in lieu of propylene glycol and 1-methanol, respectively, and 1 g of diclofenac sodium was uniformly dispersed.

COMPARATIVE EXAMPLE 4

A diclofenac sodium plaster containing 1 mg of diclofenac sodium per cm$^2$ was obtained in a similar manner to Example 4 except that purified water was added instead of propylene glycol and 1-menthol and 1 g of diclofenac sodium was uniformly dispersed.

Test 1

The diclofenac sodium plasters prepared in Example 1 and Comparative Examples 1, 2 and 3, respectively, were each applied to the shaved backs (30 cm$^2$ area) of three male guinea pigs (species: Hartley, age: 4 weeks old, body weight: 250–300 g). From each guinea pig, blood samples were collected through a cannula inserted in the carotid before the application of the plaster and upon elapsed times of 2, 4, 6 and 8 hours after the application of the plaster. The diclofenac concentrations in the plasmas of the respective blood samples were measured by HPLC, whereby changes in the diclofenac sodium concentration in plasma were observed. The results are diagrammatically shown in FIG. 1.

Test 2

Figure 2:
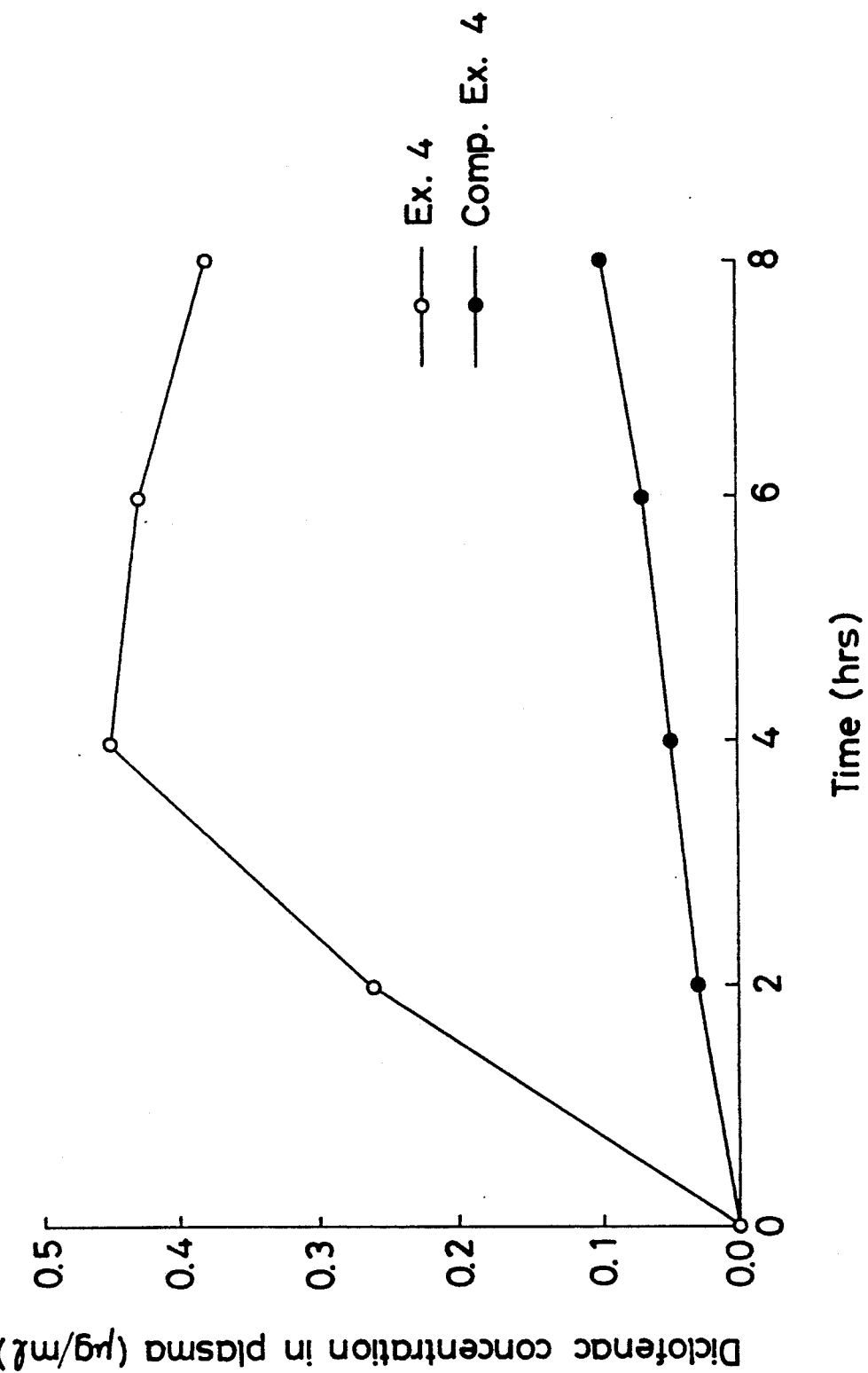
FIG. 2 diagrammatically illustrates time-dependent changes in the diclofenac concentration in plasma when the diclofenac sodium plasters prepared in Example 4 and Comparative Examples 4, respectively, were applied.

The diolofenao sodium plasters prepared in Example 4 and Comparative Example 4, respectively, were each applied to the shaved backs (30 cm$^2$ area) of three male guinea pigs (species: Hartley, age: 4 weeks old, body weight: 250–300 g). From each guinea pig, blood samples were collected through a cannula inserted in the carotid before the application of the plaster and upon elapsed times of 2, 4, 6 and 8 hours after the application of the plaster. The diclofenac concentrations in the plasmas of the respective blood samples were measured by HPLC, whereby changes in the diclofenac sodium concentration in plasma were observed. The results are diagrammatically shown in FIG. 2.

We claim:

1. A diclofenac sodium plaster comprising a backing material and a paste spread on the backing material, said paste comprising diclofenac sodium, a penetration enhancer composed of 1-menthol and propylene glycol, and a hydrophilic base composed principally of a water-soluble polymer, wherein diclofenac sodium is contained in an amount of 0.5–20 wt. % based on the paste, wherein the water-soluble polymer is contained in an amount of 0.5–40 wt. % based on the paste, wherein propylene glycol is contained in an amount of 0.1–60 wt. % based on the paste, wherein 1-menthol is contained in an amount of 0.05–10 wt. % based on the paste, and wherein the backing material is a woven or non-woven fabric of rayon, polyester, polyolefin or polyurethane fibers, a polymer film, or a foamed sheet.

2. The plaster of claim 1, wherein the water-soluble polymer is selected from the group consisting of polyacrylic acid, sodium polyacrylate, carboxyvinyl polymer, sodium carboxymethylcellulose, polyvinyl pyrrolidone, polyvinyl alcohol, hydroxypropylcellulose, hydroxyethylcellulose, ethylcellulose, alginic acid, sodium alginate, and gelatin.

3. The plaster of claim 1, wherein the stress of the paste ranges from $5 \times 10^3$ to $5 \times 10^5$ dyne/cm$^2$.

* * * * *